United States Patent
Lavin, Jr.

(10) Patent No.: US 6,514,279 B1
(45) Date of Patent: Feb. 4, 2003

(54) APPARATUS FOR EFFECTING BODY TEMPERATURE CHANGES

(75) Inventor: Edward F. Lavin, Jr., Houston, TX (US)

(73) Assignee: Personal Climate Control, Inc., Houston, TX (US)

( * ) Notice: Subject to any disclaimer, the term of this patent is extended or adjusted under 35 U.S.C. 154(b) by 125 days.

(21) Appl. No.: 09/602,484

(22) Filed: Jun. 23, 2000

(51) Int. Cl.[7] .................................................. A61F 7/00
(52) U.S. Cl. ........................ 607/108; 607/112; 607/114; 607/111
(58) Field of Search ................................ 607/108, 112, 607/114, 111; 602/14

(56) References Cited

U.S. PATENT DOCUMENTS

| | | | |
|---|---|---|---|
| 4,326,533 A | 4/1982 | Henderson | 128/402 |
| 4,676,247 A * | 6/1987 | Van Cleve | 607/112 |
| 4,831,842 A | 5/1989 | Kelley et al. | 52/457.4 |
| 4,854,319 A | 8/1989 | Tobin | 128/380 |
| 4,908,248 A | 3/1990 | Nakashima | 428/355 |
| 5,005,374 A | 4/1991 | Spitler | 62/259.3 |
| 5,016,629 A | 5/1991 | Kanare | 128/402 |
| 5,050,596 A * | 9/1991 | Walasek et al. | 607/111 |
| 5,146,625 A * | 9/1992 | Steele et al. | 607/108 |
| 5,274,865 A | 1/1994 | Takehashi | 5/644 |
| 5,304,216 A | 4/1994 | Wallace | 607/112 |
| 5,400,617 A | 3/1995 | Ragonesi et al. | 62/530 |
| 5,466,251 A * | 11/1995 | Brunson et al. | 607/108 |
| 5,514,170 A | 5/1996 | Mauch | 607/109 |
| 5,733,321 A | 3/1998 | Brink | 607/111 |
| 5,766,235 A | 6/1998 | Kostopoulos | 607/114 |
| 5,840,080 A | 11/1998 | Der Ovanesian | 607/114 |
| 5,843,145 A | 12/1998 | Brink | 607/114 |
| 5,993,480 A * | 11/1999 | Burrows | 607/112 |
| 6,083,254 A * | 7/2000 | Evans | 607/108 |
| 6,108,581 A * | 8/2000 | Jung | 607/100 |
| 6,231,596 B1 * | 5/2001 | Collins | 607/114 |

OTHER PUBLICATIONS

Thermal Logic Manufacture of Hot/Cold Therapy Products, <http://www.thermal–logic.com> visited Sep. 20, 2000.
Article entitled "Glove Power", p. 26, 28 & 33; Sports Illustrated, Jun. 19, 2000.
The Sharper Image Aug. 1999 Catalog—Cover pg, Back pg, Page including item #SI528—Personal Cooing System.
The Sharper Image Oct. 2000 Catalog, Cover Pg; Back Page, p. 38 which includes Item #SI528—Personal Cooling System.
The Sharper Image Oct. 2000 Catalog, p. 63.

* cited by examiner

Primary Examiner—Linda C. M. Dvorak
Assistant Examiner—Jocelyn Ram
(74) Attorney, Agent, or Firm—Robert C. Shaddox

(57) ABSTRACT

A band is provided for effecting body temperature changes, locally as well as core body temperature changes. The band includes a shell containing and easily replaced thermal insert filled with a high thermal capacity substance, and may also include thermal insulation, a radiant barrier, or an insulating airs space in order to increase thermal efficiency. The band may be strapped or otherwise attached to a user's body, preferably inside the forearms, directly over the wrists, where core body temperature changes may be effected.

27 Claims, 7 Drawing Sheets

APPARATUS FOR EFFECTING BODY TEMPERATURE CHANGES

FIELD OF THE INVENTION

The present invention relates in general to devices for cooling and warming, and more particularly, for effecting body temperature changes in humans who wear or apply such a device to the body.

BACKGROUND OF THE INVENTION

It is well known that humans who are engaged in strenuous activity, such as sports, may undergo a detrimental body temperature increase, and associated fatigue and decreased performance. Similarly, it is also well known that in cold climates, human body temperature may decrease as a result of environmental exposure, also resulting in fatigue and the potential for serious injury. Depending on atmospheric and environmental conditions, a normal human heat transfer function may be assisted, under these and other environmental conditions, by directly applying warm or cold substances to the body in order to effect a local temperature differential, and thus, heat transfer.

In addition, it is well known that direct application of heat or cold to various injuries, especially stress injuries to muscles, joints, and tendons, may provide a therapeutic effect.

For example, athletes engaged in sporting activities often apply ice packs during periods of rest in order to cool themselves and regain strength for continued activity. In addition, a common therapy for stress injuries to a limb or joint often includes a first application of ice packs directly to the injured limb or joint, as well as a later application of heat via electric heating pad.

There are several known prior art devices for effecting cooling or warming the human body. For example, U.S. Pat. No. 5,766,235 to Kostopoulos discloses a shallow, insulative pouch containing a removable cooling pack for keeping the inside of a user's wrists cool during physical activity. Similarly, U.S. Pat. No. 5,514,170 discloses a cold pack device for extending around a body part in a self-supporting manner, the cold pack including an insulative housing to retain a cold pack, and straps for securing the cold pack to a user's head or upper arms.

The thermal efficiency of these prior art devices varies widely. Under circumstances in which a plentiful supply of hot or cold substances exist, or where an external power supply is nearby, thermal efficiency may not be a concern. However, under circumstances in which the supply of hot or cold substances is limited or where there is no nearby power source, e.g., during activities such as hiking, biking, or running, thermal efficiency of such a warming or cooling device is a principal concern. In these activities, highly efficient warming or cooling devices are required in order to provide relatively long duration heat transfer.

Another important consideration in the implementation of warming or cooling devices is how easily and securely the device may be worn while engaged in strenuous activity. Bulky or protruding devices restrict movement of the wearer and may add unnecessary weight, thus detrimentally affecting human performance and increasing the likelihood that such devices will not be worn long enough to achieve the desired result.

Like other sporting or therapeutic devices, ease of operation, rapid recharging, and durability are also factors that influence the effectiveness of warming or cooling devices. Warming or cooling devices intended for use by persons, whether during strenuous activity or while at rest, should thus be easy to operate, simple to recharge with a fresh warming or cooling source, and be durable and secure so as to withstand rapid movements and enable prolonged and repeated use.

SUMMARY OF THE INVENTION

Body temperature changes are effected by the apparatus of the present invention through the use of a shell containing an easily replaced thermal insert. The thermal insert contains a high thermal capacity substance. The shell containing the thermal insert may be strapped or otherwise secured in place on the body, preferably on the forearms, directly over the wrists. A temperature gradient between the warmed or chilled thermal insert causes desirable heat transfer between the body and thermal insert.

Efficiency of the band is improved by locating a layer of thermal insulation, a radiant barrier, or an insulating air space between the high thermal capacity substance and the environment.

Effectiveness of the band is greatly improved by locating the band in a preferred position directly over the wrists, where heat transfer is effected between the thermal insert and the tissue underlying the wearer's forearm, including the wearer's radial arteries and nearby blood veins. Thus, the band of the present invention not only causes a local temperature change of the tissue underlying the wearer's forearm, but also desirably causes a global, body core temperature change. This dual temperature change caused by the band of the present invention, as used in the preferred position thereby facilitates reducing heat-related fatigue and improving long-term performance.

Ergonomics and ease of use of the band of the present invention is improved by incorporating elastic and absorbent cuffs, as well as by employing a concave bottom surface and a rounded end portion of the shell (either of which aiding use of the band in the preferred position as discussed herein).

The foregoing has outlined the features and technical advantages of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following description, taken in conjunction with the accompanying drawings, in which.

DETAILED DESCRIPTION OF THE PREFERRED EMBODIMENT

Figure 2:
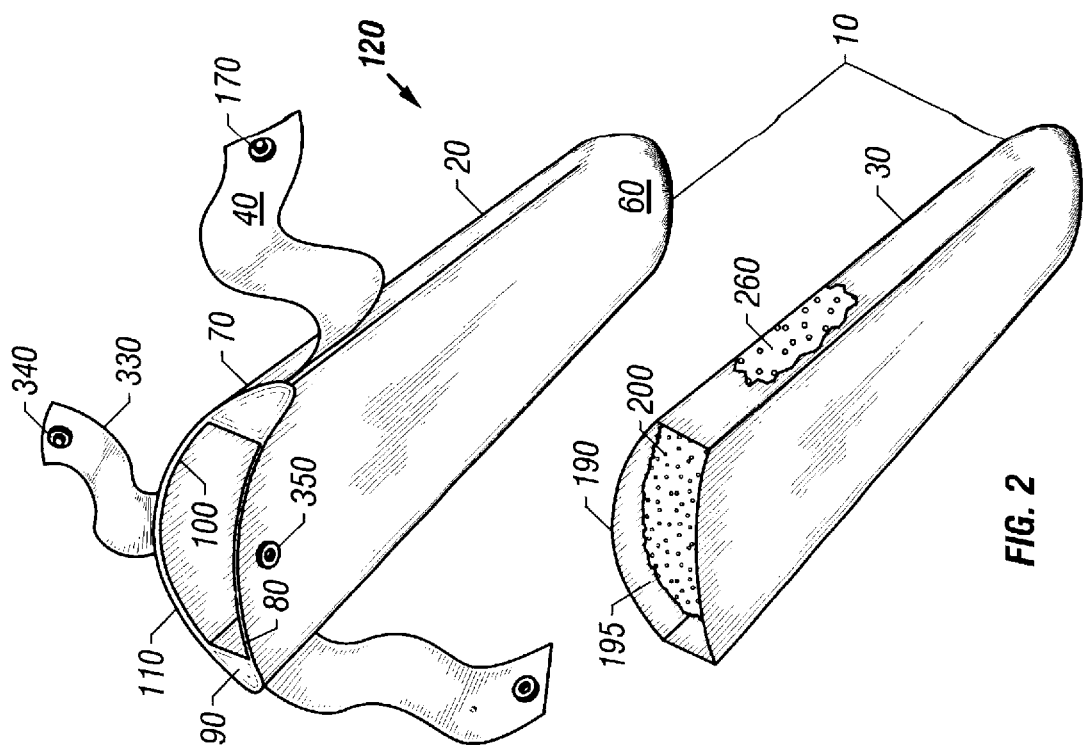
FIG. 2 is a perspective view of an embodiment of the band of the present invention, illustrating the thermal insert removed therefrom.

Refer now to the drawings, wherein the depicted elements are not necessarily shown to scale and wherein like or similar elements are designated by the same reference numeral through the several views.

Figure 1:
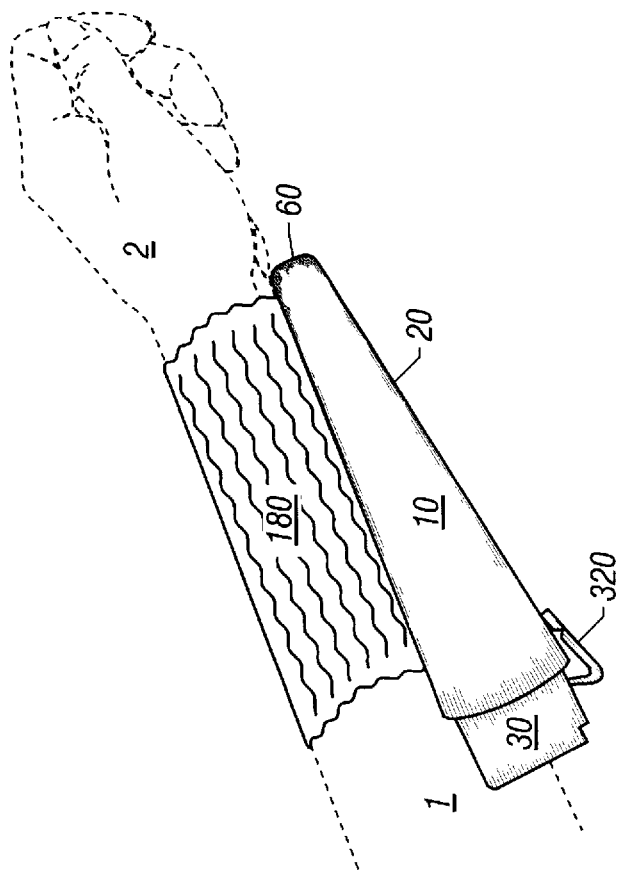
FIG. 1 is a side view of an embodiment of the band of the present invention, shown worn about the left forearm of a human.

In FIG. 1 there is illustrated a warming or cooling band 10 according to the present invention. FIG. 1 provides a broad overview of the band, which is shown worn about the left forearm 1 of a human, near a left wrist 2. The band includes two basic components: a shell 20 which forms a pocket, and a thermal insert 30 (shown partially removed from the shell 20). The thermal insert 30 includes a high thermal capacity substance that retains heat or cold (not shown) such that the thermal insert 30 may be warmed or chilled. Heat transfer between the human and the band 10 is effected by placing the band 10 in contact with the body, preferably on one or both forearms 1. The band 10 is shown in FIG. 1 being held in place by a cuff 180. In FIG. 2, the band 10 includes a strap 40 or plurality of straps 40 for holding band 10 in a desired location.

Although the band 10 is shown in FIG. 1 worn about a left forearm 1, it should be understood by those skilled in the art to which the present invention pertains that the band 10 could be worn or placed at practically any point on the body. Moreover, those skilled in the art would recognize that the cuff 180 or strap 40 could be easily modified to secure the band 10 to most any such point on the body, as discussed in more detail below. In addition, it should be understood that the strap 40 and cuff 180 could be omitted entirely in situations where the band 10 may be held in position manually, for example, for localized warming during periods of rest. Nonetheless, it may be desired to provide such a means for securing band 10 in place even during periods of rest, for example, when band 10 is worn while sleeping.

In the preferred position, as shown in FIG. 1, band 10 is worn near the end of one or both forearms 1, over the wrist 2, so that heat transfer is effected as near as possible to the wrists 2. This position of band 10 provides an optimum location for potential body temperature-altering heat transfer. In this position, the band 10 covers a substantial length of the wearer's radial artery (not shown), as well as numerous co-located, near-surface blood veins. Thus, general heat transfer, as well as body core temperature alterations, may be obtained (as opposed to merely local heat transfer and local tissue temperature alterations).

This preferred position of band 10 on forearm 1 indicated in FIG. 1 has been found particularly effective when band 10 is worn during sports or other strenuous activity, where heat induced fatigue is reduced and long-term physical performance improvements may be achieved. By way of example, activities in which band 10 may be used include sports, such as biking, running, tennis, football, and golf; strenuous work, such as in gardening, construction, and mail delivery; outdoor activities in which cooling or warming may be desired, such as motorcycling and hiking; and where indoor environmental control is not possible, such indoors during hot days without air conditioning.

For applications in which band 10 is worn on forearm 1, over wrist 2, band 10 also includes a substantially rounded portion, hereinafter the closed end 60. The inclusion of substantially rounded closed end 60 has been found to decrease the interference of band 10 with rotation of the nearby joint of wrist 2, thus enhancing ergonomics and ease of operation.

FIG. 2 illustrates the basic components of one embodiment of the band 10. There is shown the shell 20 and the thermal insert 30. The thermal insert 30 is further shown removed from the shell 20 to illustrate its details.

Shell 20 is preferably formed from a plastic, polycarbonate, thermoplastic elastomer, fiber composite, or rubber material, although those skilled in the art would recognize that many other durable materials could be substituted. For uses of band 10 during exceedingly rugged activities, fiber composite materials may prove advantageous; however, for most activities including sports, moldable plastics, thermoplastics, and rubber materials have proven effective. Where plastic or other moldable materials are used, the shell 20 may be molded according to otherwise well known manufacturing techniques.

In general, the shell 20 forms a pocket for receiving the thermal insert 30.

The shell includes a top portion 70, a bottom portion 80, the closed end 60, and an open end 90. As shown in FIG. 1, the bottom portion 80 of the shell 20 contacts the skin of forearm 1 or other extremity of the wearer. Additionally, since most surfaces of the body are generally convex, the bottom portion 80 of shell 20 is may also be concave so as to provide the broadest possible area of contact with convex body parts, such as forearm 1 and wrist 2.

As is discussed below in more detail, with reference to FIG. 2, the top portion 70 of shell 20 includes an interior surface 100 and an exterior surface 110, the exterior surface 110 facing (or being exposed to) an environment 120, and the interior surface facing (or being exposed to) the thermal insert 30.

For cooling applications, heat transfer is effected from the area of body underlying the band 10, through the bottom portion 80 of shell 20, and to the chilled thermal insert 30. For warming applications, heat transfer is effected from the warmed thermal insert 30, through the bottom portion 80 of shell 20, and to the area of the body underlying the band 10. The heat transfer relationship for both cooling and warming applications is simplified herein by considering heat in both cases to transfer from the thermal insert 30, through the bottom portion 80 of shell 20, and to the area of the body underlying the bottom portion 80 of shell 20.

Figure 2A:
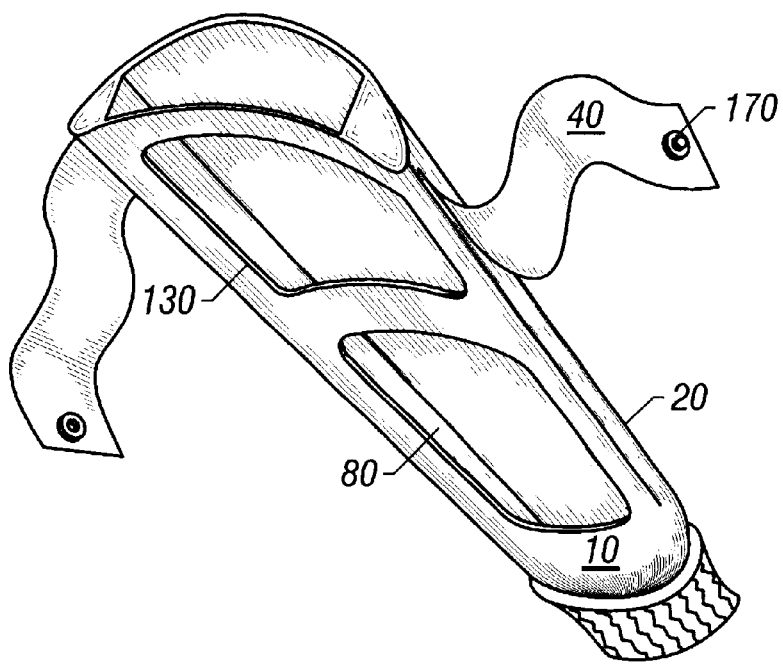
FIG. 2A is a perspective view of an alternative embodiment of the shell of the present invention.
Figure 2B:
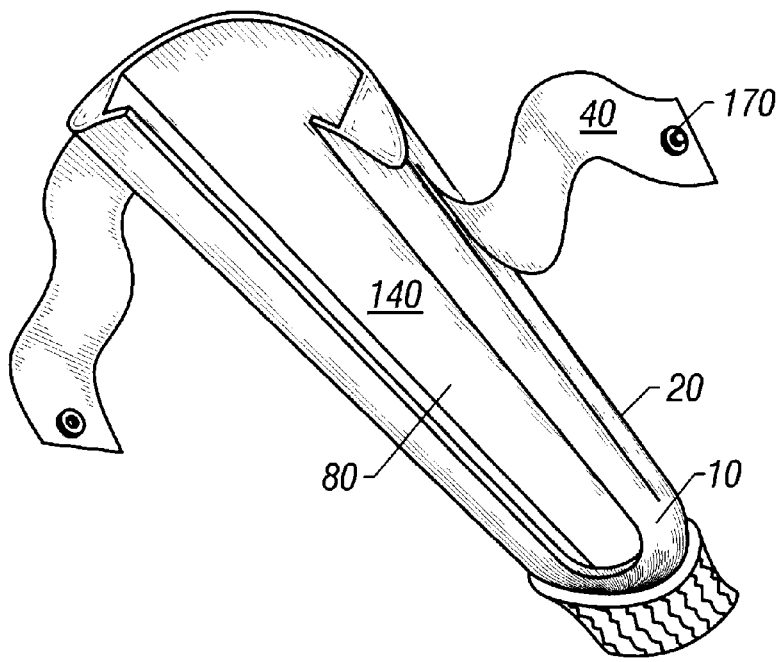
FIG. 2B is a perspective view of an alternative embodiment of the shell of the present invention.

For both warming and cooling applications, it is desirable to provide a bottom portion 80 of shell 20 that is thermally conductive. This may be achieved by one of several means. The bottom portion 80 of shell 20 may be formed from a material of high thermal conductivity, e.g., metallic substances. Alternatively, the bottom portion 80 of the shell 20 may be formed from a less thermally conductive material, but thinned so as to provide less insulating effect. Another alternative would be forming the bottom portion 80 of the shell 20 so as to extend only partly around the thermal insert 30, either by providing relatively large open spaces 130 in the bottom portion 80 (as is shown in FIG. 2A), or by leaving a relatively large area 140 of the bottom portion open (as is shown in FIG. 2B).

Figure 3:
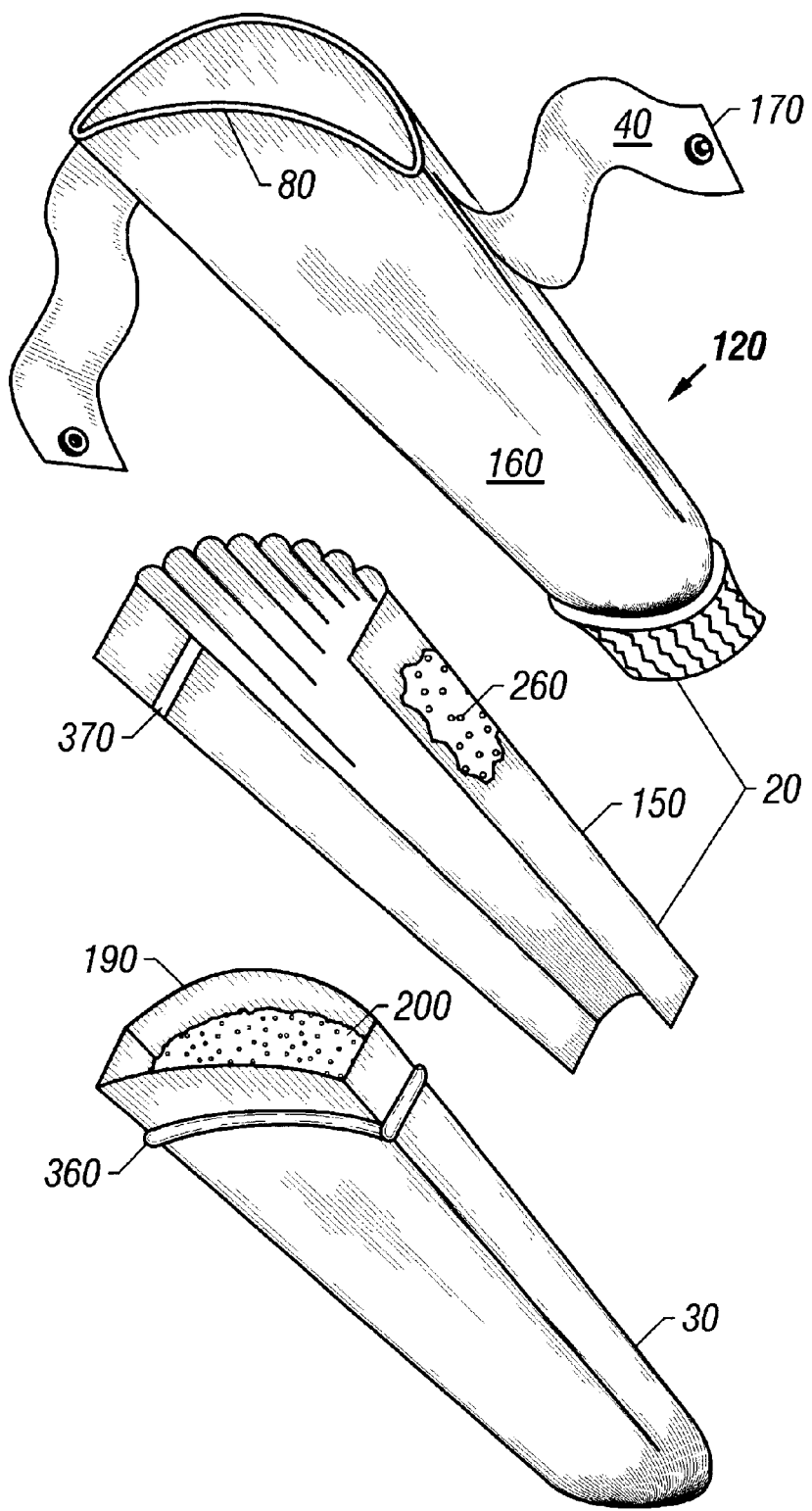
FIG. 3 is a perspective view of an alternative embodiment of the present invention.

A fourth alternative to forming a thermally conductive bottom portion 80 is shown in FIG. 3. Here, shell 20 comprises two components: a rigid inner shell 150 and a flexible outer shell 160. The rigid inner shell 150 extends only partly around thermal insert 30, whereas the flexible outer shell 160 substantially covers the inner shell 150 and forms bottom portion 80. In this alternative, different materials may be used to form the two components of the shell 20. A rigid material, such as plastic or fiber composites, could be used to form the inner shell 150, and flexible, less thermally conductive and thinner materials, such as low durometer rubber, could be used to form the outer shell 160.

Referring again to FIG. 2, there is shown the open end 90 of shell 20, which is situated adjacent to the top portion 70 and the thermally conductive bottom portion 80, open end 90 being adapted to removably receive the thermal insert 30 within the pocket formed by shell 20.

The closed end 60 of shell 20 opposes the open end 90, as shown in FIG. 2. As previously mentioned, for generalized cooling applications, band 10 is desirably located on forearm 1, preferably as near as possible to the wearer's wrist 2. However, in this position, band 10 may interfere with flexibility and range of movement of the wearer's wrist 2. It is therefore desirable to substantially round the edges of the closed end 60 of shell 20 in order to permit a wider range of wrist flex and mobility than would be present if the closed end 60 of shell 20 were substantially square.

Where it is desired to secure band 10 in place on the body, especially during physical activity, such as in sports, it is desirable to provide a means for securing the band 10 in close proximity to the body. Many different means for accomplishing this securing function could be employed, either separately or in combination. Referring again to FIG. 2, such a means for securing the band 10 in close proximity to the body could be formed by extending a strap 40 or plurality of straps 40 from the shell 20 to surround and grip an extremity. Straps 40 may be formed from fabric, rubber, plastic, or other flexible material, and are shown in FIG. 2 extending from the shell 20. When a strap 40 or plurality of straps 40 are employed, the means for securing the band in close proximity to the body may also include fasteners 170, which could be most any common strap fastener, e.g., Velcro®, snaps, buttons, standard or quick-release buckles, or latches.

The means for securing the band to the body might also include a cuff 180 or plurality of cuffs 180 extending from the shell 20 and around the extremity, as shown in FIG. 1. An elastic cuff 180 or plurality of elastic cuffs 180 could be used so that the band 10 may be slipped over the end of the extremity, for example, slipped over a hand and held in place on the forearm 1 with the closed end 60 of shell 20 directly over the wrist 2. When the band 10 is worn during sporting or strenuous activities, it may be desirable to include one or more flexible and absorbent cuffs 180 to act both as a means for securing the band, and to absorb both perspiration and any moisture that forms on band 10 resulting from physical activity or condensation. Four-way stretch terry-cloth material, such as is used in wrist bands for sporting activities, has been found particularly effective for forming the one or more cuffs 180. Under circumstances when one or more cuffs 180 are employed to secure band 10, the material forming cuff 180 may be attached to shell 20 by any standard technique known to those of ordinary skill in the art, e.g., stitching or bonding.

Referring again to FIG. 2, thermal insert 30 includes a casing 190 that forms an interior cavity 195 adapted for containing a high thermal capacity substance capable of retaining heat or cold for relatively long periods, for example, at least 30 minutes, and preferably at least 60 minutes. The thermal insert 30, casing 190, and high thermal capacity, heat-retaining substance are discussed below in more detail.

As mentioned, thermal insert 30 includes a casing 190, which may be formed from practically any durable material. Efficiency, ease of manufacturing, and expense considerations suggest the use of plastics, fiber composites, or metallic materials for creating the casing 190. Where plastics or other moldable materials are used, the casing may be injection molded or blow molded, in relatively the same manner as discussed above in connection with the shell 20. However, resistance of casing 190 to leaks may be improved by utilizing blow molding techniques.

Many varied liquids, gels, solids, and combinations thereof are suitable for use as the high thermal capacity, heat-retaining substance located within the cavity 195 formed by the casing 190 of thermal insert 30, as would be recognized by one skilled in the art to which the present invention pertains. As used herein, it should be understood that the term heat-retaining substance would also include substances that retain cold. Examples of such high thermal capacity, heat-retaining substances suited for applications in which band 10 is used for warming would include, silica, cross-linked polymers, thermal gels or colloid suspensions, and grains. Examples of such high thermal capacity, heat-retaining substances suited for applications in which band 10 is used for cooling would include water (ice), thermal gels or colloids, grains, or cross-linked polymers.

Many of such heat-retaining substances are either sold commercially or found within commercially available heating or cooling devices, for example, Blue Ice® and Hot Ice™ products manufactured by Rubbermaid Home Products, Wooster, Ohio; Crylon™- or Cryogel™-filled products by various manufacturers; heating or cooling devices containing cross-linked polymers offered by Thermal Logic, Inc., Bastrop, La.; or TA7 thermal gel manufactured by Concept Chemicals, Inc. of Houston, Tex. For simplicity, all such high thermal capacity, heat-retaining substances shall hereinafter be referred to as a thermal gel 200, as indicated in FIG. 2.

The thermal insert 30 containing thermal gel 200 is heated or chilled prior to using band 10 for warming or cooling an extremity. Depending on the capabilities and limitations of the particular thermal gel 200 chosen for use within the casing 190 of thermal insert 30, different methods of heating or chilling may be employed. According to these capabilities and limitations, which are well known within the art, the thermal insert 30 containing thermal gel 200 might be heated by immersing it in hot water or placing it in a microwave, whereas it might be chilled by placing it a freezer or immersing it in ice water.

For situations in which band 10 is used overextended periods, for example, during golf games or construction work, and the temperature of thermal insert 30 approaches body temperature, band 10 may be recharged. Here, band 10 may remain in place, while freshly warmed or cooled thermal inserts 30 may be inserted within shell 20. Freshly warmed or cooled thermal inserts 30 may be kept nearby band 10 during use, for example, in a nearby freezer or portable cooler (not shown). In this manner, the desirable body temperature changes provided by band 10 may be prolonged almost indefinitely.

Thermal insert 30 may be held in place during use of band 10 of the present invention, within the pocket formed by shell 20, by any one of several means recognizable by one of ordinary skill in the art with reference to this specification. By way of example, and not by limitation, FIG. 1 illustrates a latch 320, which removably locks the thermal insert 30 within shell 20. Alternatively, FIG. 2 illustrates a second strap 330 and second fasteners 340 and 350, which, in conjunction, removably strap the thermal insert 30 within shell 20.

FIG. 3 provides yet another alternative to securing thermal insert 30 within shell 20. Here, an o-ring 360 encircles thermal insert 30. O-ring 360 deforms when slipped within a corresponding groove 370 within inner shell 150, thus locking thermal insert 30 within shell 20 by o-ring 360 returning to its initial shape.

A temperature gradient created between the warmed or cooled thermal insert 30 and the environment 120 typically causes undesirable heat transfer between the thermal gel 200 and the environment 120, as well as desirable heat transfer between the thermal gel 200 and the body. As would be recognized by one of ordinary skill, the warming or cooling capacity of the thermal gel 200 is not unlimited. Therefore, band 10 of the present invention optionally provides various means for insulating the thermal gel 200 from the environment 120 in order to increase the efficiency and the effective duration of use of band 10.

Figure 4A:
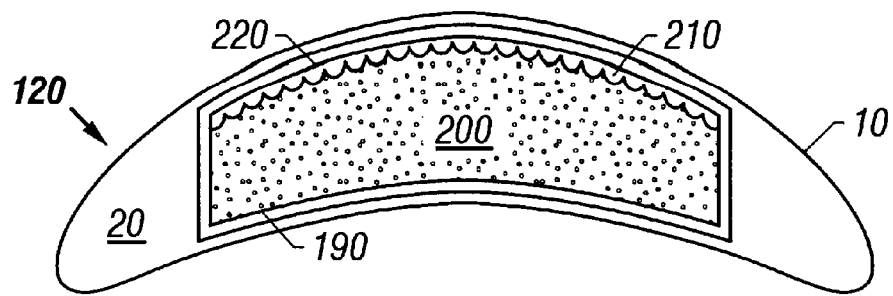
FIGS. 4A through 4D are cross-sectional views, viewed from above, of one embodiment of the thermal insulation in the band of the present invention.
Figure 4B:
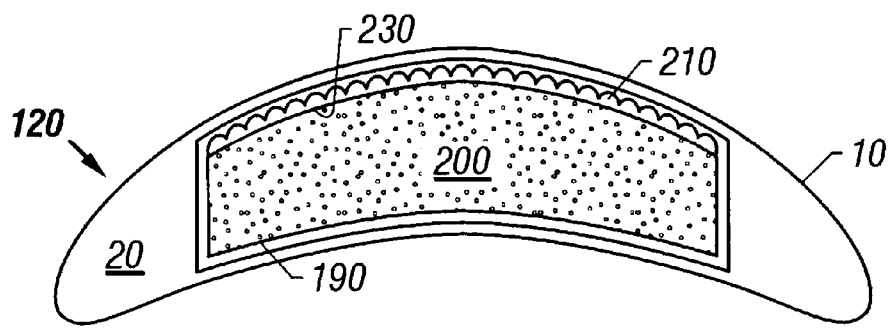
Figure 4C:
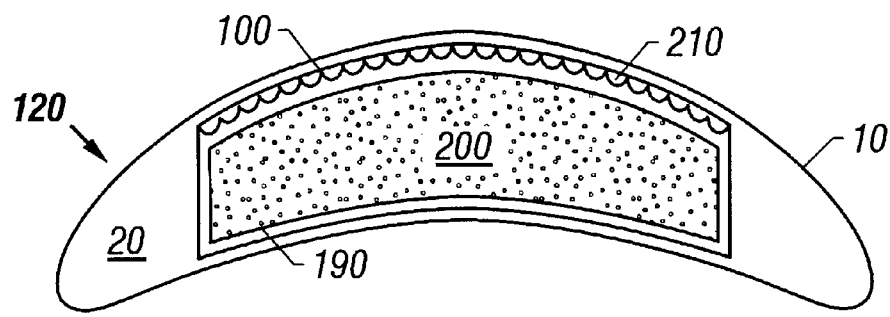
Figure 4D:
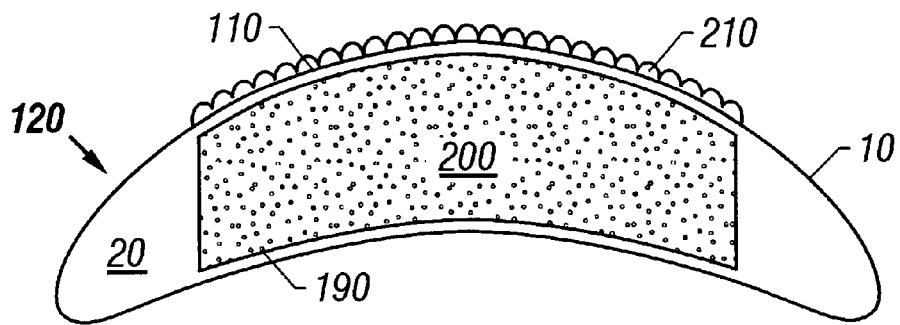

First, with reference to FIGS. 4A through 4C, if it is desired to increase the thermal efficiency of band 10, thermal insulation 210 may be located between thermal gel 200 and the environment 120. Those skilled in the art, with reference to this specification, will appreciate that insulation 210 may be any standard insulating material placed at any location on band 10 between the thermal gel 200 and the environment 120, and will thus achieve the desired result of increasing the thermal efficiency and effective duration of use of band 10. For example, insulation 210 may be any one of the many forms of fibrous insulations or insulating foams. Insulation 210 might be located in one of several locations, including: (a) on an inner surface 220 or outer surface 230 of casing 190 (FIGS. 4A and 4B, respectively); (b) on the interior surface 100 or exterior surface 110 of the top portion 70 of shell 20 (FIGS. 4C and 4D, respectively); (c) on the closed end 60 or open end 90 of shell 20 (not shown); (d) on either distal end of casing 190 (not shown); or (e) on any combination of the foregoing locations. Insulation 210 should not be provided on the bottom portion 80 of shell 20 (shown in FIGS. 1 and 2).

Figure 5A:
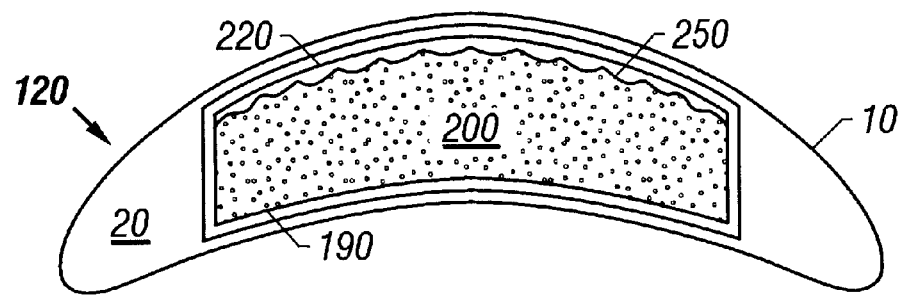
FIGS. 5A through 5D are cross-sectional views, viewed from above, of another embodiment of the thermal insulation, the radiant barrier, in the band of the present invention.
Figure 5B:
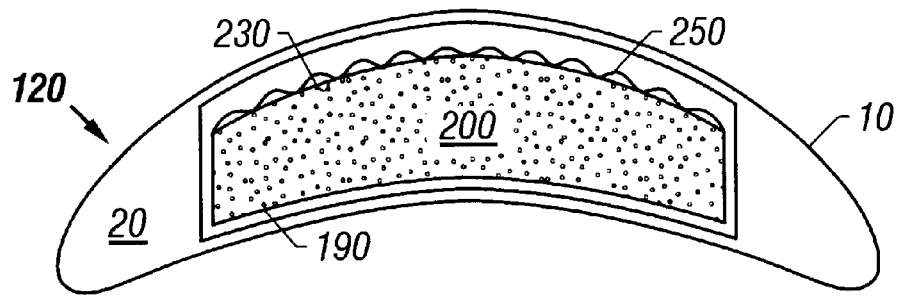
Figure 5C:
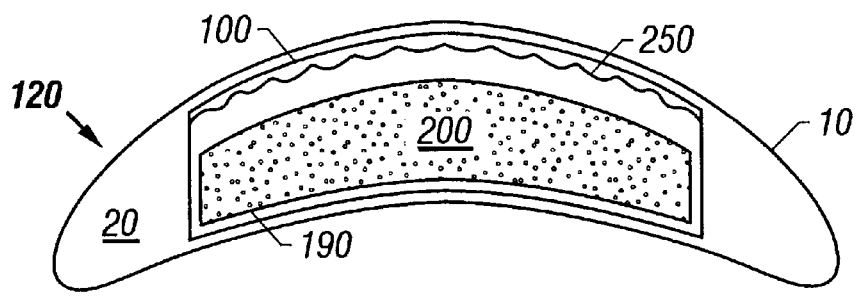
Figure 5D:
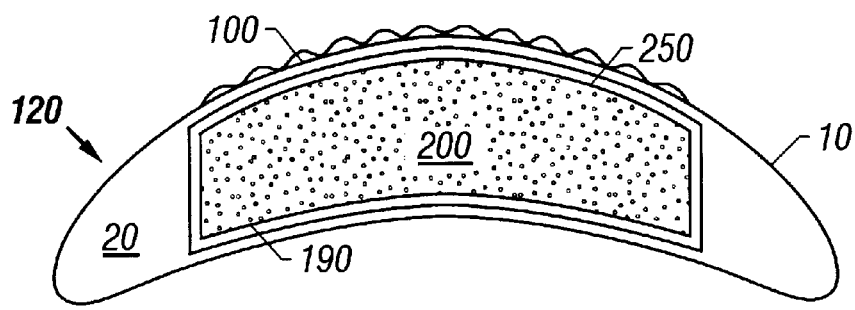

Second, with reference to FIGS. 5A through 5D, if it is desired to further increase the thermal efficiency of the band 10, a radiant barrier 250 may be positioned between the thermal gel 200 and the environment 120. Several methods may be employed to create and position the radiant barrier 250. Like the insulating methods discussed above, the radiant barrier 250 may be positioned practically anywhere between the thermal gel 200 and environment 120, so that it might prevent undesirable radiant heat transfer from the thermal gel 200 to the environment 120. As such, radiant barrier 250 may be located at any one or more of the following locations: (a) one the inner surface 220 or outer surface 230 of casing 190 (FIGS. 5A and 5B, respectively); (b) on the interior surface 100 or exterior surface 110 of shell 20 (FIGS. 5C and 5D, respectively); (c) on the closed end 60 or open end 90 of shell 20 (not shown); or (d) on either distal end of casing 190 (not shown). Radiant barrier 250 should not be provided on the bottom portion 80 of shell 20 (shown in FIGS. 1 and 2).

Examples of suitable radiant barriers may include Mylar or other metallic foils, films, or metal vacuum deposition materials; bright white color coatings; or bright metallic flakes. By way of example, the cutaway portion of FIG. 2 illustrates metallicflakes 260 shown included within the plastic material forming the casing 190 of thermal insert 30. In another example, the cutaway portion of FIG. shows metal flakes 260 included within the plastic material forming the inner shell 150.

When moldable materials are used to form the casing 190, shell 20, inner shell 150, or outer shell 160, metallic flakes 260 forming the radiant barrier 250 may be included within the moldable materials by mixing the metallic flakes directly with plastic material, either as the plastic is manufactured, or as it is being molded into its desired shape during manufacture. The Magnapearl 2000 and Magnapearl 4000 products manufactured by RTP Company of Winona, Minn. are suitable examples of metallic flakes 260.

Figure 6A:
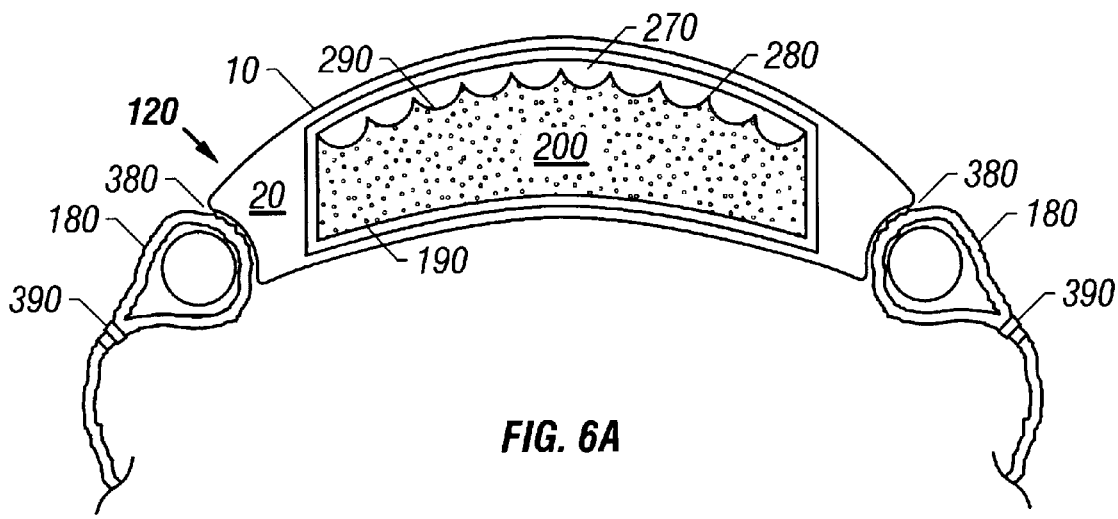
FIGS. 6A through 6D are cross-sectional views, viewed from above, of yet another embodiment of the thermal insulation, the insulating air space, in the band of the present invention.
Figure 6B:
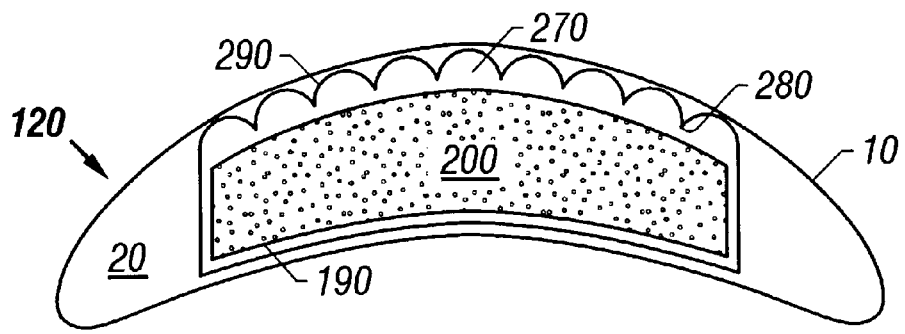

Third, with reference to FIGS. 6A through 6D, if it is desired to even further increase the thermal efficiency of band 10, an insulating air space 270 may be formed between the outer surface 230 of casing 190 and the interior surface 100 of the top portion 70 of shell 20. Several methods may be employed to create the insulating air space 270. For example, a plurality of ridges 280 may be formed along the length of casing 190 (FIG. 6A), or along the interior surface 100 of the shell 20 (FIG. 6B). In this manner, a plurality of insulating air spaces 270 are created between the relatively large valleys 290 formed between the relatively small ridges 280, whether the ridges 280 are formed on the casing 190 (FIG. 6A), or on the interior surface 100 of shell 20 (FIG. 6B).

Figure 6C:
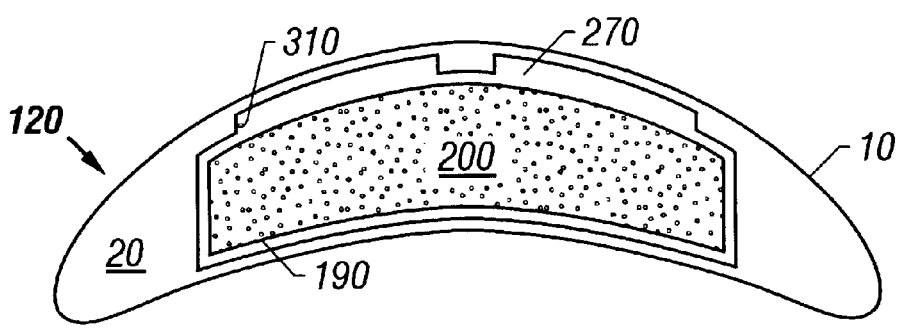
Figure 6D:
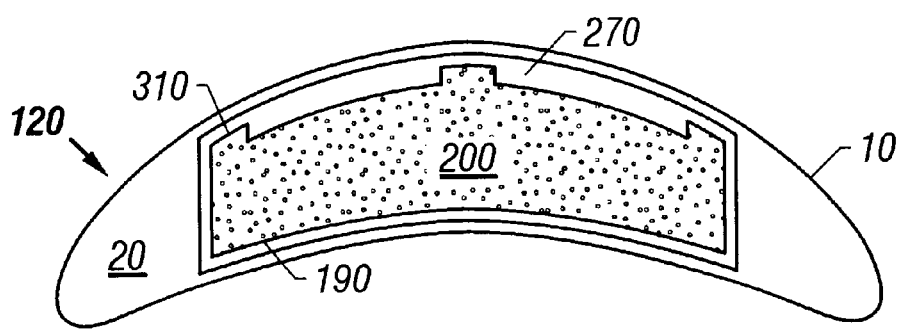

Alternatively, as shown in FIGS. 6C and 6D, the insulating air space 270 may be formed by locating a plurality of relatively small protrusions 310, either on the casing 190 or on the interior surface 100 of the top portion 70 of shell 20 (shown in FIGS. 6C and 6D, respectively). Those skilled in the art would recognize, with reference to this specification, that other methods for creating such an insulating air space 270 may be employed with equal effectiveness, and without departing from the spirit and scope of the present invention.

Among the many alternative configurations and methods of manufacture described herein for making the present invention, one configuration and corresponding method of manufacture has been proven particularly effective for use of band 10 in the preferred position. Referring to FIGS. 1 and 3, this particularly effective configuration and method of manufacture includes employing the two-piece configuration for shell 20. Inner shell 150 is formed from a substantially rigid plastic material, and impregnated with the previously mentioned Magnapearl 2000 or 4000 metal flakes by mixing the metal flakes, shown by reference numeral 260 in FIG. 3, directly with the plastic material during an injection molding process. Flexible outer shell 160 is formed from a low durometer synthetic rubber material and is overmolded directly over inner shell 150, thus providing a relatively thin, flexible and concave bottom: portion 80 well suited for matching the surface of forearm 1. While shell 20 could be easily adapted to form a different shape to match a left and a right forearm 1, a single shape for shell 20 has been found both effective and simpler to manufacture.

In the particularly effective configuration and method of manufacture, thermal insert 30 is formed from a plastic material through blow molding techniques to form ridges, as indicated by ridges 280 in FIG. 6A. For cooling applications, thermal insert 30 is then filled by gravity feeding the previously mentioned TA7 thermal gel and plugged by any standard technique well known to those skilled in the relevant art. Thermal insert 30 forming a cavity 195 of approximately 40 cubic centimeters, the cavity 195 being filled with TA7 gel, has been found to provide at least 60 minutes of cooling, under normal conditions experienced during exercise or for general cooling applications.

Lastly, with reference to FIG. 1, the particularly effective configuration for band 10 includes a single cuff 180 extending substantially the whole length of shell 20, the cuff 180 being formed from a four-way stretch terry-cloth material and slightly tapered to match the taper of a standard forearm 1, as indicated in FIG. 1. As shown in FIG. 6A, the cuff 180 is desirably attached to shell 20 by looping the material forming cuff 180 through slots 380 in shell 20, and stitching the material at stitches 390 placed along the length of cuff 180.

Accordingly, the present invention provides an apparatus for effecting body temperature changes whereby a heating or cooling band, the band including a shell forming a pocket therein retaining a heated or chilled thermal insert, is placed in contact with the body, preferably at a pulse point on an extremity of the body, in order to effect heat transfer in an efficient and effective manner between the heated or chilled thermal insert and the body.

Although the present invention and its advantages have been described in detail, it should be understood that various changes, substitutions, and alterations can be made herein without departing from the spirit and scope of the invention as defined by the appended claims.

What is claimed is:

1. A band for effecting body temperature changes, the band comprising:
    a shell including
        a top portion,
        a thermally conductive bottom portion, and
        an open end adjacent to the top portion and the bottom portion, such that the shell
        forms a pocket adapted for placement on a wearer's body;
    a thermal insert positioned within the pocket and beneath the top portion of the shell, the thermal insert further comprising
        a casing forming a cavity therein, and
        a thermal gel within the cavity such that heat transfer may be effected between the thermal gel and the wearer's body; and
    thermal insulation between the thermal gel and an environment, wherein the thermal insulation includes an insulating air space formed by a plurality of ridges or localized protrusions that extend between the casing and the top portion of the shell, thereby insulating the thermal gel from the environment.

2. The band of claim 1 wherein the thermal insulation further comprises an insulating radiant barrier formed between the thermal gel and the environment.

3. The band of claim 1 wherein the insulating radiant barrier includes a metallic layer.

4. The band of claim 1 wherein the insulating radiant barrier includes a plurality of metallic flakes.

5. The band of claim 1 further comprising a means for securing the band in close proximity to the wearer's body.

6. The band of claim 5 wherein the means for securing the band includes a strap extending from the shell, the strap being adapted for removably strapping the band to the wearer's body.

7. The band of claim 5 wherein the means for securing the band includes an elastic cuff extending from the shell.

8. A band for effecting body temperature changes, the band comprising:
    a shell forming a pocket, the shell further comprising
        a top portion,
        a thermally conductive bottom portion,
        an open end adjacent to the top portion and the bottom portion, and
        a substantially rounded closed end substantially opposing the open end;
    a removable thermal insert positioned within the pocket, the thermal insert further comprising
        a casing forming a cavity therein, and
        a thermal gel within the cavity;
    thermal insulation between the thermal gel and an environment, wherein the thermal insulation includes an insulating air space formed by a plurality of ridges or localized protrusions that extend between the casing and the top portion of the shell, thereby insulating the thermal gel from the environment; and
    a means for securing the band in close proximity to an extremity on a wearer's body, such that heat transfer may be effected from the thermal gel, through the bottom portion of the shell, and to the wearer's body.

9. The band of claim 8 wherein the thermal insulation includes an insulating radiant barrier formed between the thermal gel and the environment.

10. The band of claim 9 wherein the insulating radiant barrier includes a plurality of metallic flakes.

11. The band of claim 9 wherein the insulating radiant barrier includes a metallic layer.

12. The band of claim 9 wherein the means for securing the band includes a strap extending from the shell, the strap being adapted for removably strapping the band to the extremity.

13. The band of claim 9 wherein the means for securing the band includes an elastic cuff extending from the shell, the elastic cuff being adapted for removably gripping the bottom portion of the shell in contact with the extremity.

14. A band for effecting body temperature changes, the band comprising:
    a shell forming a pocket, the shell further comprising
        a top portion;
        a concave bottom portion, the bottom portion being thermally conductive;
        an open end adjacent to the top portion and the bottom portion; and
        a substantially rounded closed end substantially opposing the open end;
    a thermal insert positioned within the pocket, the thermal insert further comprising
        a casing forming a cavity therein, and
        a thermal gel within the cavity;
    thermal insulation between the thermal gel and an environment, wherein the thermal insulation includes an insulating air space formed by a plurality of ridges or localized protrusions that extend between the casing and the top portion of the shell, thereby insulating the thermal gel from the environment; and
    a means for securing the band on a wearer's forearm with the closed end near a wrist, such that heat transfer may be effected from the thermal gel, through the bottom portion of the shell, and to the wearer's body.

15. The band of claim 14 wherein the thermal insulation includes an insulating radiant barrier formed between the casing and the top portion of the shell.

16. The band of claim 15 wherein the insulating radiant barrier includes a metallic layer.

17. The band of claim 15 wherein the insulating radiant barrier includes a plurality of metallic flakes.

18. The band of claim 14 wherein the means for securing the band includes a strap extending from the shell, the strap being adapted for removably strapping the band so that the bottom portion of the shell contacts the wearer's forearm and the closed end of the shell is near the wearer's wrist.

19. The band of claim 14 wherein the means for securing the band includes an elastic cuff extending from the shell, the elastic cuff being adapted for removably securing the band so that the bottom portion of the shell contacts the forearm and the closed end of the shell is near the wrist.

20. A band for effecting body temperature changes, the band comprising:
a flexible outer shell forming a pocket, the outer shell further comprising
a top portion,
a thermally conductive bottom portion,
an open end adjacent to the top portion and the bottom portion, and
a rounded closed end substantially opposing the open end;
a substantially rigid inner shell including an open end, the inner shell being located within the outer shell and adjacent to the top portion of the outer shell;
a thermal insert positioned within the pocket and within the inner shell, the thermal insert being selectively removable from the pocket through the open end of the inner shell and the outer shell, the thermal insert further comprising
a casing forming a cavity therein, and
a thermal gel within the cavity;
thermal insulation between the thermal gel and an environment, such that heat transfer between the thermal gel and the environment may be retarded; and
an elastic cuff extending from the outer shell, the elastic cuff being adapted for removably securing the band so that the bottom portion of the outer shell contacts a wearer's forearm and the closed end of the outer shell is near a wearer's wrist.

21. The band of claim 20 wherein the thermal insulation further includes an insulating air space formed between the thermal gel and the environment.

22. The band of claim 21 wherein the insulating air space is formed by a plurality of localized protrusions between the casing and the top portion of the shell.

23. The band of claim 21 wherein the insulating air space is formed by a plurality of ridges between the casing and the top portion of the shell.

24. The band of claim 20 wherein the thermal insulation includes a metallic radiant barrier.

25. The band of claim 24 wherein the insulating radiant barrier includes a plurality of metallic flakes dispersed within, the material forming the inner shell.

26. The band of claim 25 wherein the thermal insulation includes an insulating air space formed by ridges extending between the thermal insert and the inner shell, the ridges being generally aligned with the longitudinal axis of the band.

27. The band of claim 20 wherein the thermal insulation further includes an insulating radiant barrier formed by a plurality of metallic flakes.

* * * * *